(12) United States Patent
Hotta (10) Patent No.: US 10,031,088 B2
(45) Date of Patent: Jul. 24, 2018

(54) MEASUREMENT APPARATUS

(71) Applicant: FUJI XEROX CO., LTD., Tokyo (JP)

(72) Inventor: Hiroyuki Hotta, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 15/492,412

(22) Filed: Apr. 20, 2017

(65) Prior Publication Data

US 2017/0356852 A1    Dec. 14, 2017

(30) Foreign Application Priority Data

Jun. 13, 2016 (JP) ................ 2016-116874

(51) Int. Cl.
   *G01N 21/00* (2006.01)
   *G01N 21/89* (2006.01)
   *G01N 21/93* (2006.01)
(52) U.S. Cl.
   CPC ..... *G01N 21/8901* (2013.01); *G01N 21/8903* (2013.01); *G01N 21/93* (2013.01)
(58) Field of Classification Search
   CPC .... G01N 21/55; G01N 21/553; G01N 21/211; G01N 21/253; G01N 21/47; G01N 21/9501; G01N 21/552; G01N 21/6456; G01N 21/65; G01N 21/956; G01N 2201/0221; G01N 33/54373; G01N 2021/213; G01N 21/01
   See application file for complete search history.

(56) References Cited

U.S. PATENT DOCUMENTS

| 2009/0238590 A1* | 9/2009 | Masuda | G03G 15/0178 399/49 |
| 2010/0266302 A1* | 10/2010 | Suzuki | G01N 21/55 399/49 |
| 2016/0153903 A1* | 6/2016 | Ono | G01N 21/474 356/432 |

FOREIGN PATENT DOCUMENTS

| JP | 2002-209839 A | 7/2002 |
| JP | 2009-284959 A | 12/2009 |
| JP | 2010-197931 A | 9/2010 |

* cited by examiner

*Primary Examiner* — Michael P Stafira
(74) *Attorney, Agent, or Firm* — Sughrue Mion, PLLC (57) ABSTRACT

A measurement apparatus includes:
   plural light emitting units that generate irradiation light to be emitted to an object;
   a light receiving unit that receives reflected light of the irradiation light that is projected to the object and reflected, and outputs a reflected light amount;
   a moving unit that performs a relative movement so as to cause the object and the irradiation light to move relative to each other; and
   a controller that performs a control to execute a first measurement and a second measurement.

9 Claims, 9 Drawing Sheets

MEASUREMENT APPARATUS

CROSS-REFERENCE TO RELATED APPLICATIONS

This application is based on and claims priority under 35 USC 119 from Japanese Patent Application No. 2016-116874 filed Jun. 13, 2016.

BACKGROUND

Technical Field

The present invention relates to measurement apparatus.

SUMMARY

According to an aspect of the invention, a measurement apparatus includes:
plural light emitting units that generate irradiation light to be emitted to an object;
a light receiving unit that receives reflected light of the irradiation light that is projected to the object and reflected, and outputs a reflected light amount;
a moving unit that performs a relative movement so as to cause the object and the irradiation light to move relative to each other; and
a controller that performs a control to execute a first measurement and a second measurement, wherein
the first measurement includes
acquiring an overall reflected light amount for the entire object by causing the plural light emitting units to simultaneously emit light while performing the relative movement by the moving unit, and
when an abnormal reflected light amount exists in the overall reflected light amount, specifying an abnormal light amount region of the object corresponding to the abnormal reflected light amount, and
the second measurement includes
acquiring a partial reflected light amount of the object in a scanning region that is a partial region of the object at least including the abnormal light amount region, by causing the plural light emitting units to sequentially emit light while performing the relative movement by the moving unit in the scanning region, and
measuring an abnormal region of the object using the partial reflected light amount.

BRIEF DESCRIPTION OF THE DRAWINGS

Exemplary embodiments of the present invention will be described in detail based on the following figures, wherein.

DETAILED DESCRIPTION

First Exemplary Embodiment

Figure 1:
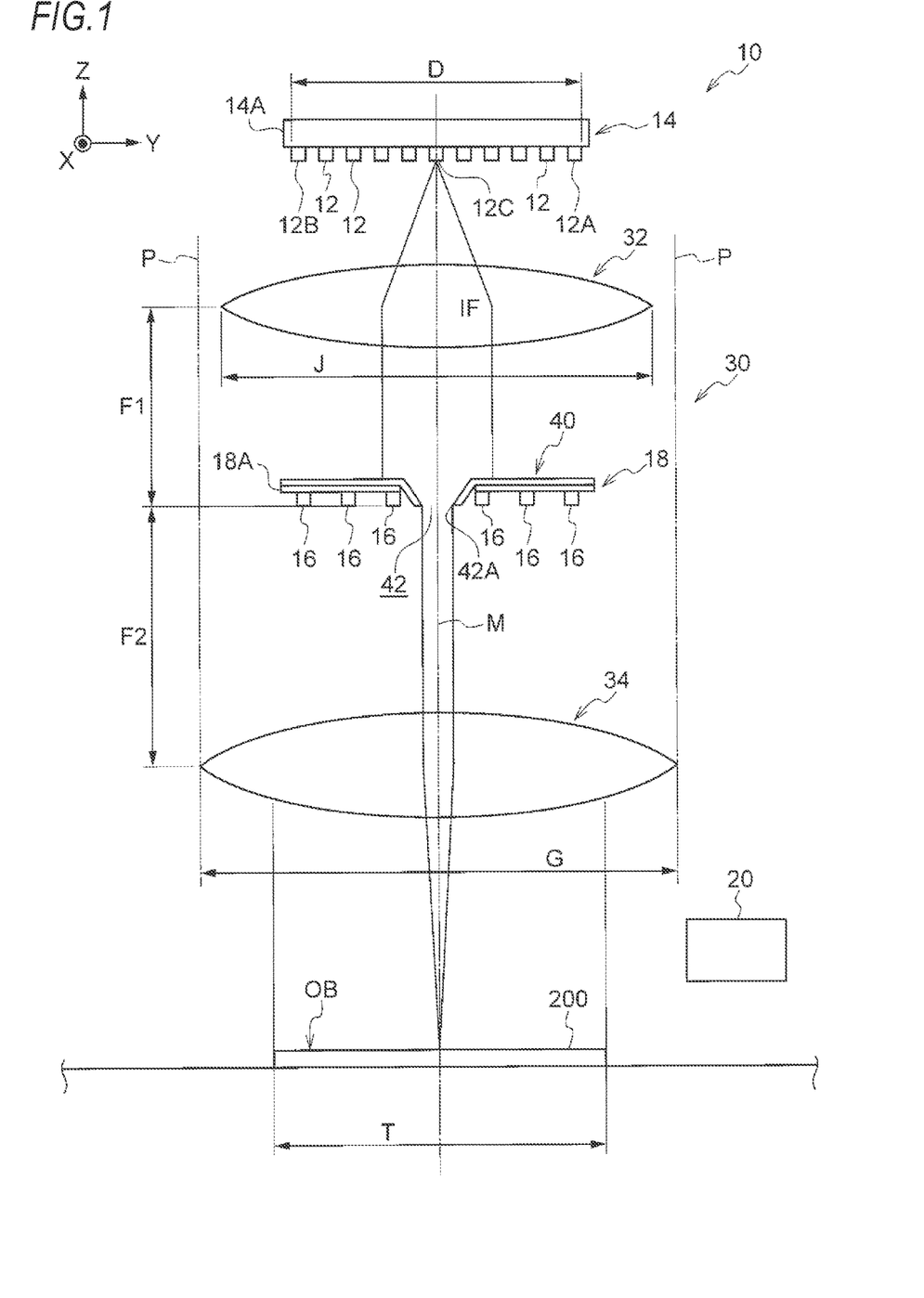
FIG. 1 is a view illustrating an example of a configuration of a measurement apparatus according to an exemplary embodiment.
Figure 2:
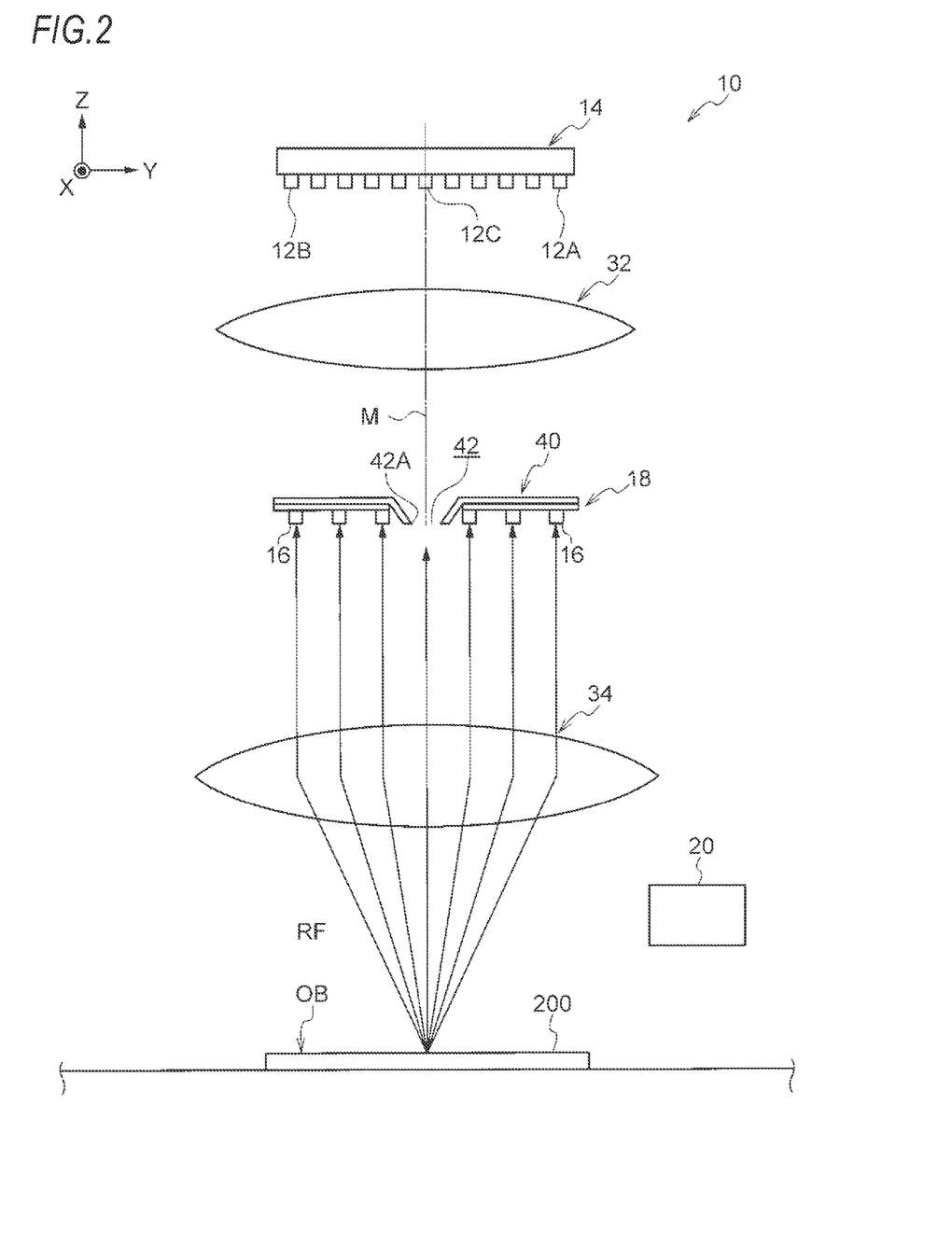
FIG. 2 is a view illustrating reflected light in the measurement apparatus according to the exemplary embodiment.

The present exemplary embodiment will be described in detail with reference to FIGS. 1 to 9. First, an example of a configuration of a measurement apparatus 10 according to the present exemplary embodiment will be described with reference to FIGS. 1 and 2. FIGS. 1 and 2 illustrate a configuration in which the measurement apparatus 10 measures an object.

As illustrated in FIG. 1, the measurement apparatus 10 includes a light emitter 14, an optical system 30, a light receiver 18, and a controller 20. The measurement apparatus 10 sequentially projects irradiation lights in a Z-axis direction to a fine region of an object OB that moves in an −X direction, and acquires a reflection angle distribution (the reflection angle dependency of a light quantity distribution) of reflected lights with respect to irradiation lights. A measure is performed without being affected by a variation in a distance from the object OB and an angle of the object OB for a change in the shape of the object OB or a surface condition (irregularity, emboss, surface roughness, surface defect, foreign matter adhesion, or the like) is measured by using the acquired reflection angle distribution.

In more detail, as illustrated in FIG. 1, the light emitter 14 is disposed at an upper side in an up and down direction (Z-axis direction) of the apparatus with respect to a measurement region T through which the object OB moving in the −X direction passes. In addition, the light emitter 14 has plural light emitting elements 12 which are mounted side by side in a Y-axis direction on a substrate 14A, and emit light in a −Z direction as a light emitting direction. In other words, the plural light emitting elements 12 are arranged in a direction orthogonal to (intersecting) the moving direction (−X direction) of the object OB. In FIG. 1, a light emitting element 12 disposed at one end portion (right end in the drawing) in the Y-axis direction of the substrate 14A is referred to as a light emitting element 12A, a light emitting element 12 is disposed at the other end portion (left end in the drawing) in the Y-axis direction of the substrate 14A is referred to as a light emitting element 12B, and the light emitting element 12 disposed at the center of the substrate 14A is referred to as a light emitting element 12C.

The plural light emitting elements 12 according to the present exemplary embodiment are configured to sequentially emit light from the light emitting element 12A to the light emitting element 12B with a time difference, and the lights from the respective light emitting elements 12 are individually projected to different positions on the object OB, respectively. In addition, the plural light emitting elements 12 are configured such that while the object OB moves in the –X direction in the measurement region T, a cycle of light emission from the light emitting element 12A to the light emitting element 12B is repeated plural times. FIG. illustrates light fluxes of an irradiation light IF when the light emitting element 12C emits light, and FIG. 2 illustrates light fluxes of the reflected light RF when the irradiation light IF emitted from the light emitting element 12C is reflected by a surface 200 of the object OB.

Although not particularly limited, for example, vertical cavity surface emitting laser (VCSEL), a light emitting diode (LED), or the like may be used as the light emitting element 12.

The optical system 30 includes a lens 32, a lens 34, and an aperture stop 40 disposed between the lens 32 and the lens 34, and is configured as a so-called double-sided telecentric lens. The optical system 30 is disposed between the light emitter 14 and the object OB, guides the irradiation light emitted from a light emitting element 12 to the object OB, and guides the reflected light reflected by the object OB to the light receiver 18. That is, the light receiver 18 is configured to receive at least a part of the light flux of the irradiation light of a light emitting element 12 after the irradiation light is emitted from the lens 34, reflected by the object OB, and then transmitted through the lens 34 again. In addition, in the present exemplary embodiment, an optical axis of the lens 32 and an optical axis of the lens 34 becomes a common optical axis M, and the optical axis M runs through the center of the light emitting element 12C of the light emitter 14 and the center of an opening 42 to be described below.

As an example, the lens 32 is a convex lens having a circular shape in a top plan view, and the diameter J of the lens 32 is greater than the size D from the light emitting element 12A to the light emitting element 12B in the Y-axis direction. For this reason, almost all the lights emitted from the respective light emitting elements 12 are transmitted through the lens 32, and the lights transmitted through the lens 32 become parallel lights by changing divergence degrees thereof to be directed toward the lens 34.

As an example, the lens 34 is a convex lens having a circular shape in a top plan view, and in the present exemplary embodiment, the diameter G of the lens 34 is greater than the diameter J of the lens 32. Further, the lens 34 condenses the light fluxes emitted from the lens 32 and transmitted through the lens 34 toward the surface 200 of the object OB. A position (focal point) of a light condensing point of the lens 34 does not always have to be a position on the surface 200 of the object OB. The position of a light condensing point may be deviated (defocused) from a position on the surface 200, and an irradiation diameter of the irradiation light IF on the surface 200, that is, a size of an irradiation region of the object OB may be adjusted. The irradiation diameter according to the present exemplary embodiment is, for example, a diameter (φ) of several tens of micrometers (μm).

A substantially circular opening 42 is formed in the aperture stop 40, and a light flux emitted from the light emitting element 12 and transmitted through the lens 32 to be incident on the lens 34 is stopped down by the opening 42. More specifically, the aperture stop 40 has a plate shape having a plate surface parallel to an X-Y plane, and a tip end portion is formed in the aperture stop 40 by being bent to be tapered toward the lens 34 around the optical axis M. This tip end portion is an opening edge 42A that defines the opening 42, and the circular shape defined by the opening 42 adopts the optical axis M as the central axis thereof. In addition, the diameter of the opening 42 according to the present exemplary embodiment is, for example, about 1 mm.

In the Z-axis direction, the distance F1 between the opening edge 42A and the lens 32 is approximately equal to the focal length f1 of the lens 32, and the distance F2 between the opening edge 42A and the lens 34 is approximately equal to the focal length f2 of the lens 34.

Figure 6A:
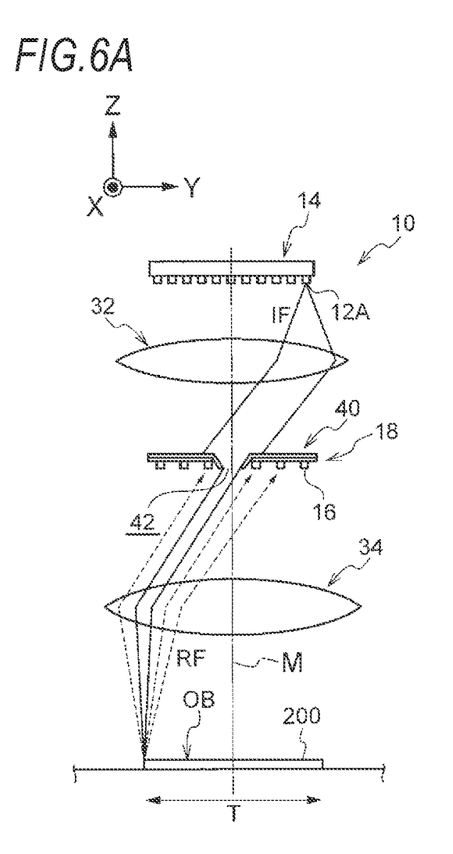
FIGS. 6A to 6C are views for explaining an operation of the measurement apparatus according to the exemplary embodiment.
Figure 6B:
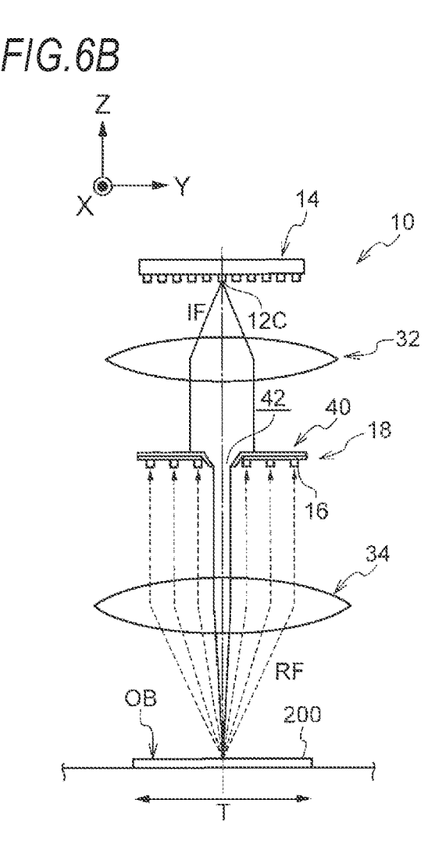
Figure 6C:
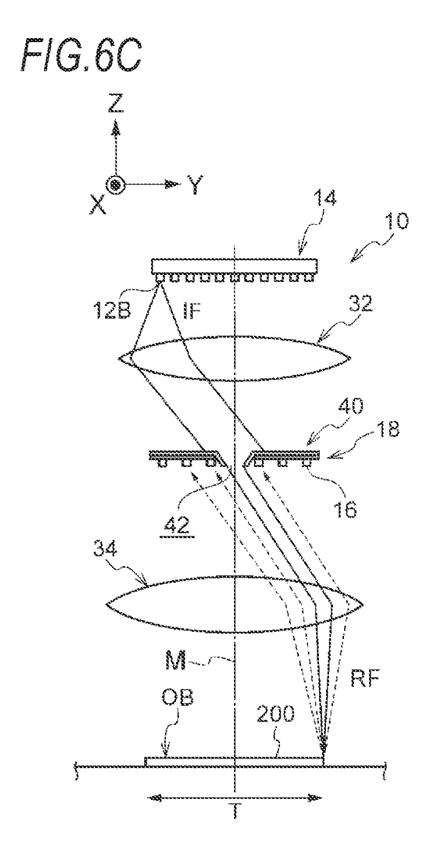

In the optical system 30 according to the present exemplary embodiment configured as described above, the light fluxes, which are sequentially emitted from the respective light emitting elements 12 are thinly stopped down, regardless of the positions of the light emitting elements 12, and are individually projected to the object OB as the irradiation lights IF parallel to the optical axis M (see FIGS. 6A to 6C). In other words, by causing the respective light emitting elements 12 to emit light for scanning, substantially circular light fluxes (spots), which are thinly stopped down and are parallel to one another, are individually projected to the object OB. In addition, in the measurement apparatus 10 according to the present exemplary embodiment, by disposing the object OB in the vicinity of the light condensing point of the light flux of the irradiation lights IF formed by the lens 34, the irradiation regions of the respective irradiation lights IF on the object OB are fine regions having substantially equal diameters. As a result, in the measurement apparatus 10, since the respective irradiation lights are projected with substantially equal irradiation diameters even though the position of the object OB is changed upward and downward in the Z-axis direction, the blurring of an image of the object OB is extremely reduced.

The light receiver 18 includes plural light receiving elements 16, and receives a reflected light RF which is reflected by the object OB and transmitted through the lens 34 of the optical system 30. The light receiver 18 according to the present exemplary embodiment is disposed at a lower side in the Z-axis direction with respect to the aperture stop 40 disposed between the lens 32 and the lens 34. Although not particularly limited, for example, a photodiode (PD), a charge coupled device (CCD), or the like may be used as the light receiving elements 16.

Since the light receiver 18 is disposed between the lens 32 and the lens 34, the light receiving elements 16 are also disposed between the lens 32 and the lens 34 similarly. Here, when the light receiving elements 16 are disposed between the lens 32 and the lens 34, it means that the light receiving elements 16 are disposed inside a cylindrical surface configured by lines P that run through outer diameter ends (virtual contact points between a radius R of a front surface and a radius R of a back surface) of the lens 34 and extend in the Z-axis direction, as illustrated in FIG. 1.

Figure 3A:
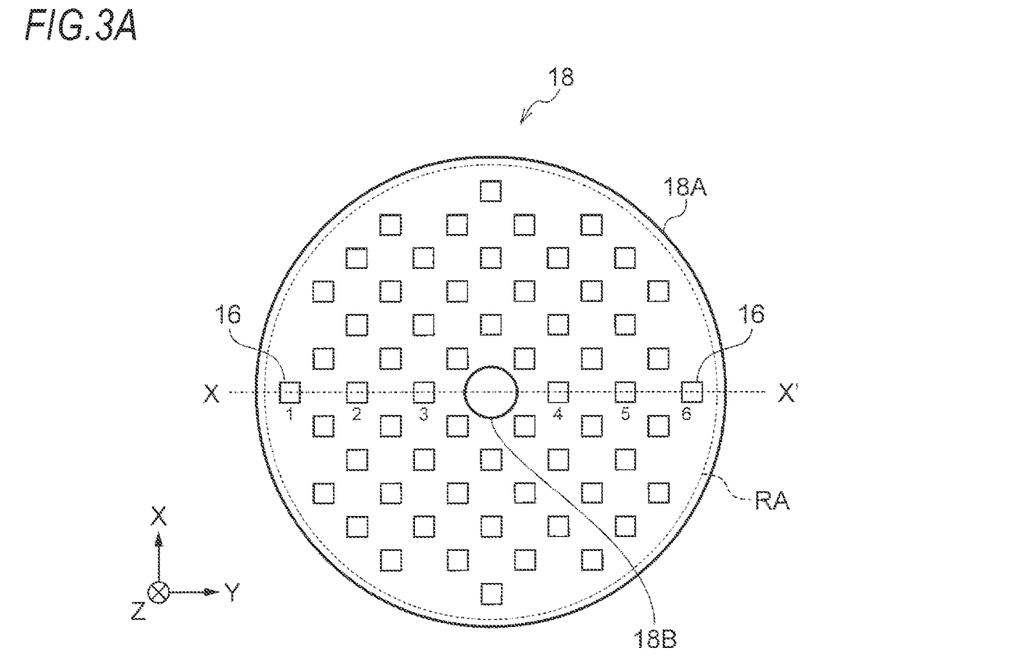
FIG. 3A is a top plan view illustrating an example of a configuration of a light receiver according to the exemplary embodiment.

FIG. 3A illustrates an example of a configuration of the light receiver 18. FIG. 3A is a top plan view of the light receiver 18 when viewed in the Z-axis direction. The light receiver 18 illustrated in FIG. 1 is illustrated in a cross-sectional view taken along line X-X' in FIG. 3A. As illustrated in FIG. 3A, the light receiver 18 is configured by disposing, for example, the plural light receiving elements 16 (e.g., FIG. 3A illustrates sixty light receiving elements) in a plane shape (array shape) on a substantially circular substrate 18A having a substantially circular opening 18B at the center thereof. The measurement apparatus 10 receives the reflected lights RF using ail of the plural light receiving elements 16 as a light receiving region RA. FIG. 3A exemplifies the light receiver 18, which has the plural light receiving elements 16 disposed on the whole surface of the substrate 18A. It should be noted that the invention is not limited thereto. The light receiver 18 may be configured such that the light receiving elements 16 are disposed on a part of the substrate 18A according to a light receiving range or the like of the reflected lights RF.

Figure 3B:
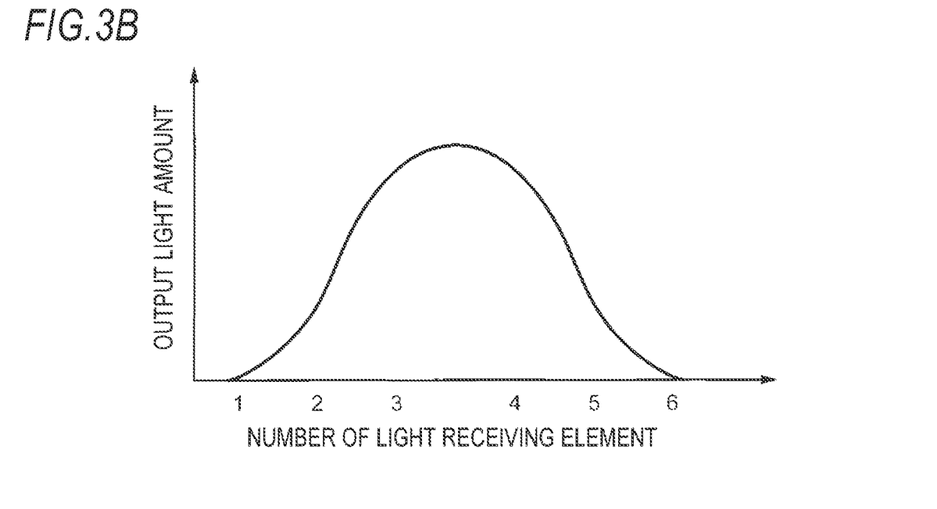
FIG. 3B is a light amount distribution of reflected light in the light receiver.

The range of the reflected light RF received in the light receiving region RA is, for example, a reflected light RF in a range of an angle of 0° to 40° centered on an axis parallel to the optical axis M. When this reflected light RF is received in the light receiving region RA, a three-dimensional distribution is formed by the received light amounts of the respective light receiving elements 16. In a case where the reflected light RF is isotropic like the light reflected by a perfect diffuse surface, the shape of a cross section of a three-dimensional distribution, which is taken along a plane including the Z axis, becomes substantially a Gaussian curve, as illustrated in FIG. 3B. In addition, numbers 1 to 6 of the light receiving elements on a horizontal axis in FIG. 3B correspond to numbers 1 to 6 of the light receiving elements 16 illustrated in FIG. 3A. In addition, an actual output distribution is discrete because no reflected light RF is received between two adjacent light receiving elements 16 in the light receiving region RA, which is omitted from FIG. 3B.

In the measurement apparatus 10, because the light receiving surface of the light receiving element 16 and the opening edge 42A are positioned at the same position in the Z-axis direction, the distance F2 between the light receiving surface of the light receiving element 16 and the lens 34 is equal to the focal length f2 of the lens 34. For this reason, even though the position of the object OB is changed upward and downward in the Z-axis direction, or leftward and rightward in the Y-axis direction, and irradiation lights IF are projected from different tight emitting elements, the output distribution in the light receiving region RA is always constant as long as the projection positions of the irradiation lights IF to the object OB are the same.

In other words, assuming that a fine region having a size substantially the same as the irradiation diameter as the object OB, when the object OB moves upward and downward in the Z-axis direction, or moves leftward and rightward in the Y-axis direction, the object OB is irradiated with different irradiation lights IF from the different light emitting elements 12, and thus reflects different reflected lights RF. However, in the measurement apparatus 10 according to the present exemplary embodiment, the output distributions made by all the light receiving elements 16 included is the light receiving region RA are always the same as each other regardless of the positions at which the reflected lights RF are generated.

Figures 4, 5A:
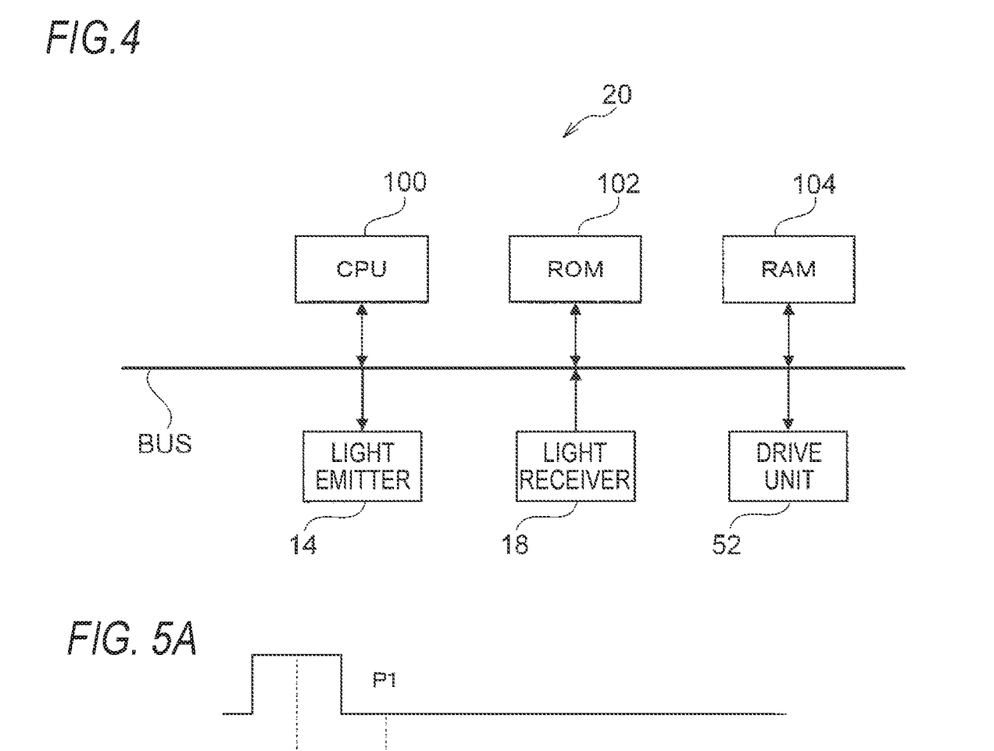
FIG. 4 is a block diagram illustrating an example of a configuration of a controller according to the exemplary embodiment.
FIGS. 5A to 5C are time charts for explaining an operation of controlling a light emitter and the light receiver according to the exemplary embodiment.

As illustrated in FIG. 4, the controller 20 includes a central processing unit (CPU) 100, a read only memory (ROM) 102, and a random access memory (RAM) 104. The CPU 100 collectively controls the entire measurement apparatus 10, the ROM 102 is a memory unit that stores is advance a control program for the measurement apparatus 10, or an abnormal spot specifying processing program or the like to be described below, and the RAM 104 is a memory unit to be used as a work area or the like when a program such as the control program is executed. The CPU 100, the ROM 102, and the RAM 104 are connected to each other through a bus BUS.

A drive unit 52, which operates a moving device (not illustrated) configured to move the light emitter 14, the light receiver 18, and the object OB, is connected to the bus BUS, and the light emitter 14, the light receiver 18, and the drive unit 52 are controlled by the CPU 100 through the bus BUS.

Figures 5B, 5C:
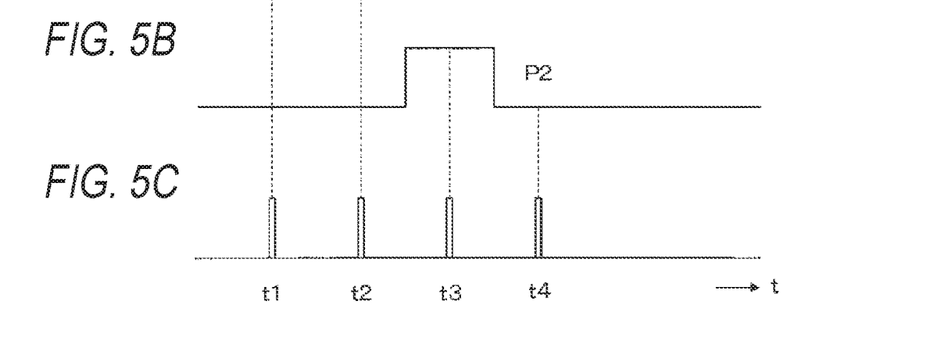

An operation of controlling the light emitter 14 and the light receiver 18 by the controller 20 will be described with reference to FIG. 5. FIG. 5A illustrates a light emitting pulse signal P1 for causing a predetermined light emitting element 12 to emit light and FIG. 5B illustrates a light emitting pulse signal P2 for causing a subsequent light emitting element 12 to emit light, in the case where the light emitting elements 12 of the light emitter 14 are caused to sequentially emit light as described above. As illustrated in FIGS. 5A and 5B, in the control of the light emitter 14 according to the present exemplary embodiment, no signal (0 level) time for a predetermined period is provided between the light emitting pulse signal P1 and the light emitting pulse signal P2 (parts corresponding to time t2 and tame t4 in FIG. 5). FIG. 5C illustrates read pulses when the light receiver 18 receives the reflected lights RF generated by the irradiation lights IF generated from the light emitting elements 12 according to the light emitting pulse signals P1 and P2. Based on the read pulses, the received light amounts of all the light receiving elements 16 included in the light receiver 18 (i.e., the light receiving elements 16 in the light receiving region RA), which becomes a signal indicating the output distribution.

First, the reflected light RF of the irradiation light IF generated according to the light emitting pulse signal P1 is read by all the light receiving elements 16 at time t1. Now, assuming that the total number of the light receiving elements 16 is k, k light receiving signals $Sr(1), Sr(2), \ldots, Sr(k)$ are acquired from the respective light receiving elements 16. Next, at time t2, the received light amount at the zero (0) level between the light emitting pulse signal P1 and the light emitting pulse signal P2 is read by all the light receiving elements 16. The k light receiving signals at the zero (0) level, which are read by all the light receiving elements 16, will be referred to as $Sr0(1), Sr0(2), \ldots, Sr0(k)$. Next, differences between the light receiving signals of the reflected light RF of all the light receiving elements 16 and the light receiving signals at the zero (0) level, that is, $Sr(1)-Sr0(1), Sr(2)-Sr0(2), \ldots, Sr(k)-Sr0(k)$ are calculated, and the k differential values are set as the output distribution of the received light amount. The output distribution is also calculated in the similar manner even after the light emitting pulse signal P2. The calculated output distribution may be temporarily stored in the memory unit such as the RAM 104.

The reason why the signals indicating the output distribution according to a reflected light RF is generated by subtracting the light receiving signals at the no signal time from the light receiving signals of the reflected light RF as described above is to eliminate an influence caused by an disturbance light. When the influence by the disturbance light is negligible, the light receiving signals of the reflected light RF may be used as they are as the signals indicating the output distribution. In this case, it is not necessary to make a space between successive light emitting pulse signals, and furthermore, since a light receiving timing is determined by the read pulses, the light emitting pulse signals may partially overlap each other.

Next, an operation of the measurement apparatus 10 when measuring a reflection property (e.g., an unevenness degree of a surface) of the object OB will be described with reference to FIGS. 6A to 6C. FIGS. 6A to 6C illustrate light flexes of the irradiation light IF in the case where the light emitting elements 12A, 12C, and 12B of the light emitter 14 sequentially emit light and the light fluxes of the reflected light RF in the case where the irradiation light IF is reflected by the surface 200 of the object OB and guided to the light receiver 18.

First, when the object OB moves in the −X direction such that the lead end of the object OB enters the measurement region T, the respective light emitting elements 12 sequentially emit light with a time difference, and the irradiation lights IF are individually projected toward the object OB. In addition, until the rear end of the object OB exits the measurement region a cycle of light emission from the light emitting element 12A to the light emitting element 12B is repeated. As described above, the light emission of the light emitting elements 12 is controlled by the controller 20.

A divergence degree of the light flux of the irradiation light IF emitted from each light emitting element 12 is changed by the lens 32 such that the light flux is directed toward the lens 34. The light flux, which has been subjected to the change of the divergence degree by the lens 32, is stopped down (restricted) by the aperture stop 40. The light flux stopped down by the aperture stop 40 is condensed by the lens 34, and projected to the object OB in the Z-axis direction (the direction parallel to the optical axis M). In other words, the object OB is disposed in the vicinity of the light condensing point of the irradiation light IF which is formed by the lens 34. The irradiation light according to the present exemplary embodiment is condensed to, for example, a diameter ($\phi$) of about several tens of micrometers ($\mu$m) on the surface 200 of the object OB as described above.

The irradiation light IF projected to the object OB is reflected by the surface 200 of the object OB, thereby generating the reflected light RF (indicated by dotted lines with arrows in FIG. 6). The directions of the light fluxes of the reflected light RF are changed by the lens 34 such that the light fluxes are directed toward the respective light receiving elements 16. The reflected light RF transmitted through the lens 34 is received by the respective light receiving elements 16.

The irradiation light IF is reflected in various directions according to the condition of the surface 200 of the object OB. However, as described above, in the present exemplary embodiment, the reflected light RF is received in the range of an angle of 0° to 40° which is centered on an axis that runs through an incident point of the irradiation light IF to the surface 200 parallel to the optical axis M. Therefore, the light receiving region RA of the light receiver 18, which corresponds to the irradiation light IF emitted from on light emitting element 12, has a substantially circular shape. FIG. 3A illustrates an example of the light receiving region RA.

The light receiving signals received by the respective light receiving elements 16 are read at a predetermined timing under the control of the controller 20 as described above. The read light receiving signals may be temporarily stored in a memory unit such as the PAM 104. The controller 20 produces an output distribution (light receiving profile) in the light receiving region PA by using the light receiving signals (brightness signals) corresponding to the respective light emitting elements 12. Because the output distribution includes angle information of the reflected light RF, for example, the unevenness degree of the object OB is measured.

As described above, according to the measurement apparatus 10 according to the present exemplary embodiment, when the reflected lights RF of the lights individually projected from the light emitting elements 12 toward the object OB are received by the light receiving elements 16, and as a result, a change in shape, a surface condition, or the like of the object OB is precisely measured.

By the way, a measurement apparatus such as the measurement apparatus 10 is often used in an actual product production line in the actual product production line, it is also required to reduce the measurement time as much as possible, as well as to perform the measurement precisely. Meanwhile, as an important application of the measurement apparatus 10 in the production line, there is an application an inspection apparatus that inspects a product for whether abnormality (defect) exists on the product, particularly, the surface of the product. Hereinafter, a case where the measurement apparatus 10 according to the present exemplary embodiment is used as an inspection apparatus that inspects whether an abnormal spot exists on the product is taken as an example, and a method of further reducing a time required for specifying an abnormal spot when the abnormal spot exists will be described.

In a case where the measurement apparatus 10 is used as an inspection apparatus, the irradiation lights IF are usually individually projected from the plural light emitting elements 12 to the object OB while moving the object OB, the reflected lights RF from the object OB is acquired throughout the object OB, and an abnormal spot on the object OB is measured by using the entire reflected lights RF. According to this inspection method, a precise measurement for a position, a range, a condition, and the like of the abnormal spot is performed.

However, the inspection method described above causes a problem in that the measurement time is increased due to the time for causing the plural light emitting elements 12 to sequentially emit light and the time for sequentially receiving the reflected light RF and processing the reflected light RF as the reflected light amount. That is, assuming that the number of the light emitting elements 12 is N, and the number of times of movement steps of the object OB in the −X direction for each measurement is M, it is required to perform the light emitting N×M times. The measurement time is determined depending on the time required for performing light emitting N×M times by the light emitting elements 12, and the time required for performing the movement steps in the −X direction M times. In addition, although the measurement time includes the processing time required for processing the light receiving elements 16 and a light receiving circuit connected to the light receiving elements 16, but in this case, the processing time is considered as being included in the light emitting time.

Meanwhile, when acquiring the reflected light amount by causing the plural light emitting elements 12 to simultaneously emit light in order to acquire the reflected light amount at once, the measurement (specifying) accuracy of an abnormal spot is deteriorated. This is due to the following reason: when the light emitting elements 12 are caused to simultaneously emit light, the reflected lights RF caused by various irradiation positions on the object OB, that is, the reflected lights RF caused by the plural light emitting elements 12 are mixed and inputted to one light receiving element 16, and as a result, the information associated with the position, the size, the condition, and the like of an abnormal spot is buried in the entire reflected light (contrast is deteriorated).

Therefore, in the present invention, the measurement of the reflected light amount is divided into two steps of a first measurement and a second measurement. That is, since the reflected light RF acquired by irradiating a defective point with the irradiation lights IF simultaneously emitted from the light emitting elements 12 (overall irradiation), is combined with the reflected lights RF of the irradiation lights IF of various directions, it is difficult to detect a defective point including an exact edge even though a broad abnormal spot including a defective spot is specified. Therefore, after a measurement is performed based on simultaneous light emission, a specified broad abnormal spot is irradiated with the irradiation light IF generated by the sequential light emission (individual irradiation), the reflected light RF reflected by the object OB is acquired by the individual irradiation, and the defective spot including an exact edge is detected by using the reflected light.

In more detail, as the first measurement, the overall reflected light amount is entirely acquired by causing the plural light emitting elements 12 to simultaneously emit light and causing the object OB to be subjected to the overall irradiation while moving the object OB in the −X direction, the existence or non-existence of an abnormality in the reflected light amount is determined using the entire reflected light amount, and a region of the object OB having an abnormality in the reflected light amount is specified as an abnormal light amount region. Next, as the second measurement, a partial reflected light amount is acquired by causing the light emitting elements 12 to sequentially emit light while moving the object OB in a scanning region including the abnormal light amount region, and the abnormal region of the object is measured (specified) in detail using the partial reflected light amount.

In the first measurement, while precise information associated with a position, a size, a condition, and the like of the abnormal spot is not acquired, the existence or non-existence of an abnormal spot and a broad region (abnormal light amount region) of the abnormal spot are determined. Further, the abnormal light amount region is acquired by M times which is the number of times of light emission corresponding to the number of steps of moving the object OB in the −X direction.

Meanwhile, in the second measurement, the partial reflected light amount is acquired by moving the object OB in the −X direction by the number of steps covering the abnormal light amount region while causing the light emitting elements 12 to sequentially emit light to be individually projected. In addition, in the sequential light emission, it is not necessary to cause all the plural light emitting elements 12 to sequentially emit light, but the light emitting elements 12, which correspond to an extent of producing the irradiation light IF covering the abnormal light amount region, may be caused to emit light. In this case, the number of light emitting elements 12 caused to emit light is set to N' (<N). In the individual irradiation, since the reflected light amount with high resolution is acquired, the precision in specifying the abnormal spot is not deteriorated, and more detail information associated with the abnormal spot on the object OB, for example, coordinates on the X-Y plane of the abnormal spot and the like are acquired.

Here, assuming that the number of movement steps in the −X direction, which covers the abnormal light amount region, is M' (<M), the number of times of light emission of the light emitting elements 12 is N'×M', and when M times of the overall irradiation is added, the number of times of light emission according to the present exemplary embodiment is (N'×M'+M). In many cases, (N'×M'+M)<N×M because M' is sufficiently compared to M. The number of movement steps in the −X direction is M in the aforementioned measurement method, and (M+M') times in the measurement method according to the present exemplary embodiment. Since M' is small, (M+M')≈M. Therefore, the measurement time of the measurement method according to the present exemplary embodiment is greatly reduced, compared with the measurement time according to the aforementioned measurement method. In the aforementioned discussion, the number of the light emitting elements 12 caused to emit light in each movement step, is always assumed to be N', but the number of light emitting elements 12 may of course be changed for each movement step. In addition, when no abnormal light amount region is detected in the first measurement, the total number of times of light emission of the light emitting elements 12 is M, and the measurement time is further reduced.

Hereinafter, an operation of the measurement apparatus 10 according to the present exemplary embodiment will be described in more detail with reference to FIGS. 7A to 8I.

Figure 7A:
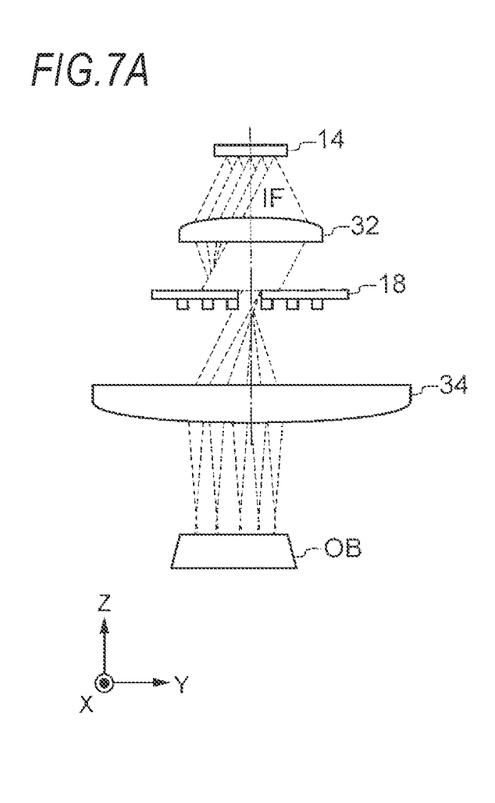
FIGS. 7A to 7C are views for explaining an operation of a measurement apparatus according to a first exemplary embodiment.

First, in the first measurement, as illustrated in FIG. 7A, the light emitting elements 12 of the light emitter 14 are caused to simultaneously emit light while moving the object OB in the −X direction in predetermined steps, and the irradiation lights IF (parallel light), which correspond to the number of light emitting elements 12, are simultaneously projected to the surface of the object OB. In the overall irradiation, the light emission of the light emitting elements 12 is basically performed while being stopped for each movement step. It should be noted that the invention is not limited thereto. The object OB may be moved in a state where the light emitting elements 12 continuously emit light. In addition, the light receiving elements 16 of the light receiver 18 receive light by adding up the reflected lights (not illustrated) generated by the irradiation lights IF, which correspond to the number of light emitting elements 12. With the overall irradiation, a reflection property throughout the object OB (a distribution of specular reflection or diffuse reflection) is output through the light receiving elements 16. FIG. 7A illustrates a case in which an abnormal light amount region (region having reflection properties different from those of other regions) is not present on the surface of the object OB.

Figure 7B:
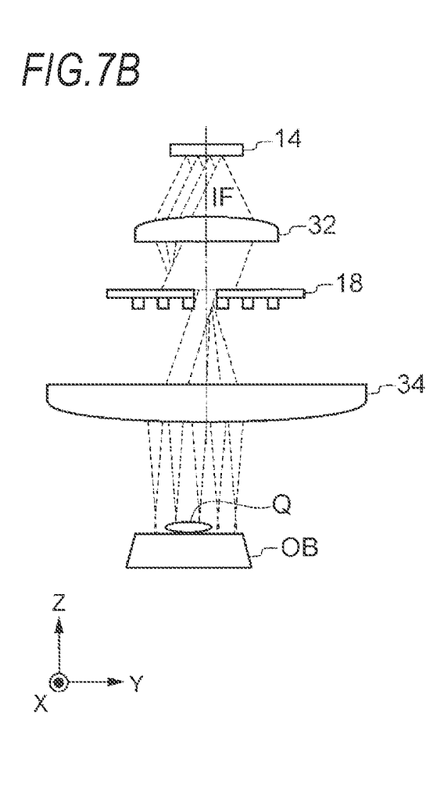

Meanwhile, FIG. 7B illustrates a case in which an abnormal light amount region Q exists on the surface of the object OB. In the case where the abnormal light amount region Q, a reflection property acquired through the light receiving elements 16 is different from that in the case of FIG. 7A. Based on the different reflection properties, the existence or non-existence of the abnormal light amount region Q is determined, and the range of the abnormal light amount region Q is acquired from, for example, coordinates on the X-Y plane. The overall irradiation is performed over the entire object OB while moving the object OB in the −X direction in a step unit in the predetermined X-axis direction.

Figure 7C:
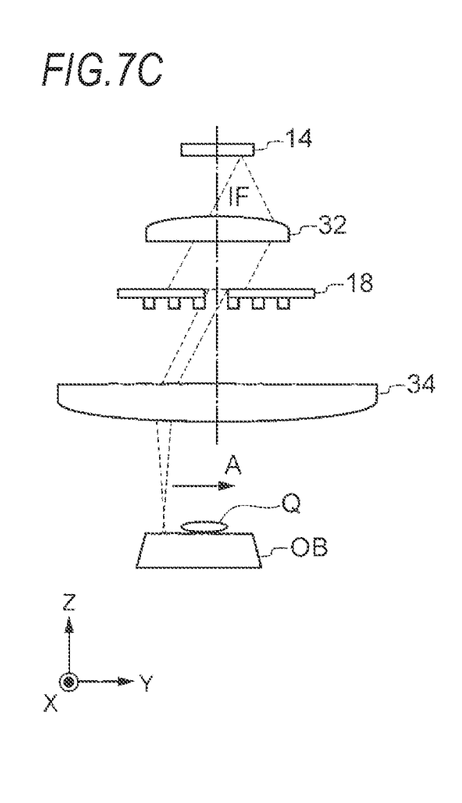

Next, in the second measurement, the object OB is moved to a position where the abnormal light amount region Q is irradiated with the irradiation light IF from the light emitter 14. In addition, as illustrated in FIG. 7C, the light emitting elements 12 of the light emitter 14 are caused to sequentially emit light, that is, the object OB is irradiated with the irradiation light IF while the irradiation light IF is moved in a direction indicated by arrow A in FIG. 7C. By acquiring reflection properties for each irradiation point through the light receiving elements 16, precise information associated with a position, a size, a condition, and the like of the abnormal light amount region Q is acquired. In addition, in the second measurement, a measurement condition for the first measurement may be changed in order to improve the measurement precision (precision in specifying a defective position). Conceivable changes include, for example, setting the movement steps in the X-axis direction more finely (e.g., to ½), and increasing the number of light emitting elements 12 caused to sequentially emit light.

In the aforementioned exemplary embodiment, descriptions have been made while exemplifying a configuration in which all the light emitting elements 12 are caused to simultaneously emit light in the overall irradiation of the first measurement. It should be noted that the invention is not limited thereto. It is possible to adopt a form in which a part of the light emitting elements 12 (e.g., every other light emitting element 12) are caused to emit light. In addition, in the aforementioned embodiment, descriptions have been made while exemplifying a configuration in which only the light emitting elements 12, which corresponds to the abnormal light amount region Q, are caused to emit light in the individual irradiation of the second measurement. It should be noted that the invention is not limited thereto. It is possible to adopt a form in which all the light emitting elements 12 are caused to sequentially emit light.

Next, irradiation light IF on the object OB will be described in more detail with reference to FIGS. 8A to 8I. FIGS. 8A to 8I exemplify the irradiation light IF when five light emitting elements 12 are caused to emit light. FIGS. 8A to 8I illustrate spots S (S1 to S5) of the irradiation light IF emitted to the object OB when viewed from the top side (Z-axis direction) of the measurement apparatus 10 illustrated in FIG. 1. FIGS. 8A to 8D illustrate states of the spots S during the first measurement, and FIGS. 8E to 8I illustrate states of the spots S during the second measurement.

In the first measurement illustrated in FIGS. 8A to 8D, the object OB moves in the −X direction according to the steps of coordinates X1, X2, X3, and X4. The spots of the irradiation light IF in the case where five light emitting elements 12 are caused to simultaneously emit light are indicated by S1 to S5. In addition, a case where five light emitting elements 12 are caused to sequentially emit light, the light emitting element 12 caused to emit light is moved in the −Y direction, and as a result, the spots S1 to S5 are moved in the +Y direction, as illustrated in FIGS. 6A to 6C. Therefore, the light emitting elements 12, which correspond to the spots S1 to S5, are indicated by y1 to y5 in sequence.

Figure 8A:
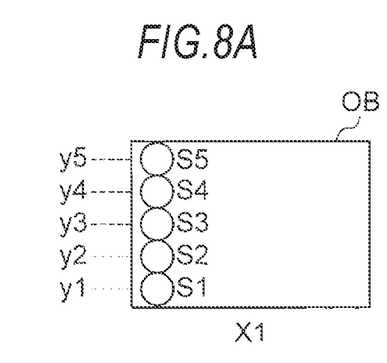
FIGS. 8A to 8I are views for explaining overall irradiation and individual irradiation according to the first exemplary embodiment.
Figure 8B:
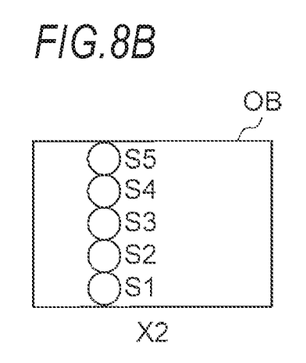
Figure 8C:
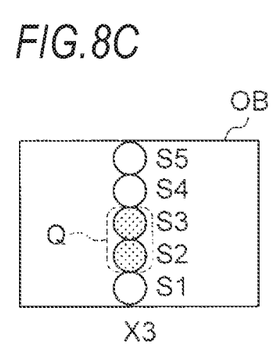
Figure 8D:
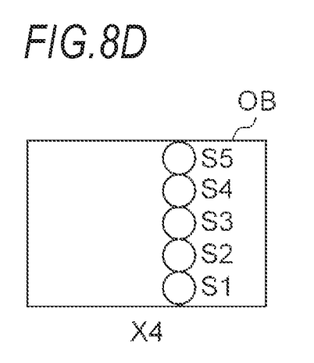
Figure 8E:
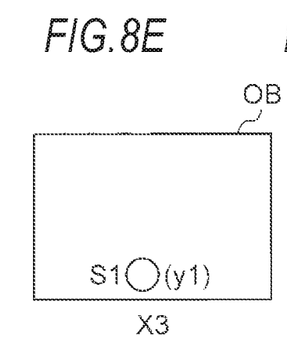
Figure 8F:
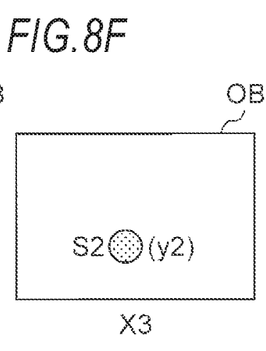
Figure 8G:
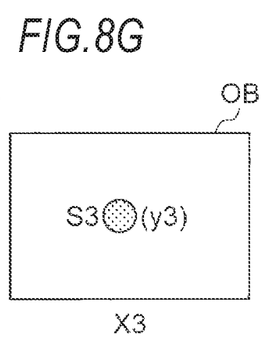
Figure 8H:
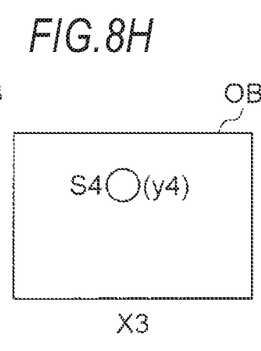
Figure 8I:
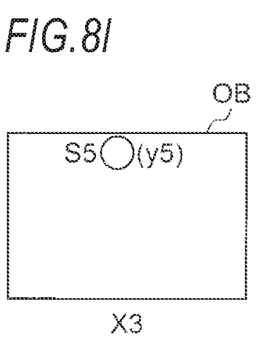

FIGS. 8A to 8D illustrate an example in which no abnormal light amount region Q is detected in the coordinates X1, X2, and X4 as illustrated in FIGS. 8A, 8B, and 8D, and the abnormal light amount region Q is detected in the coordinate X3 as illustrated in FIG. 8C. The detection of the abnormal light amount region Q is performed by comparing the received light amount of the reflected light with the predetermined reference received light amount. As illustrated in FIG. 8C, the abnormal light amount region Q is a region including the spots S2 and S3, and an output according to the first measurement is indicated by the coordinate X3. Of course, the output according to the first measurement is not limited to the coordinates of one point, and may be acquired from a range such as a range from Xmin to Xmax in some cases. However, in this step, a detail of a defect, which causes the occurrence of the abnormal light amount region Q, is not determined.

Meanwhile, in the second measurement, as illustrated in FIGS. 8E to 8I, the individual irradiation is performed by fixing the position of the object OB on the X-axis to the coordinate X3, and causing the light emitting elements y1 to y5 to sequentially emit light. With the individual irradiation, detailed information about a defect, which exists at the irradiation positions of the spots S2 and S3 that correspond to the light emitting elements y2 and y3, respectively, that is, precise information associated with a position, a size, a condition, and the like of the defect is acquired. As described above, the irradiation positions on the object OB by the light emitting elements y2 and y3 are known in advance. Therefore, by receiving the reflected light RF according to the spots S2 and S3 by the light receiving element 16, a change in shape of an abnormal (defective) point or a surface condition thereof, or the like is acquired, including the position of the abnormal spot as well. In the actual second measurement, the reflection properties may be acquired by performing the individual irradiation not only at the coordinate X3, which is an output by the first measurement, but also at coordinates before and after the coordinate X3, for example, the coordinates X2 and X4. As a result, the detection omission of a defective region is inhibited.

Figure 9:
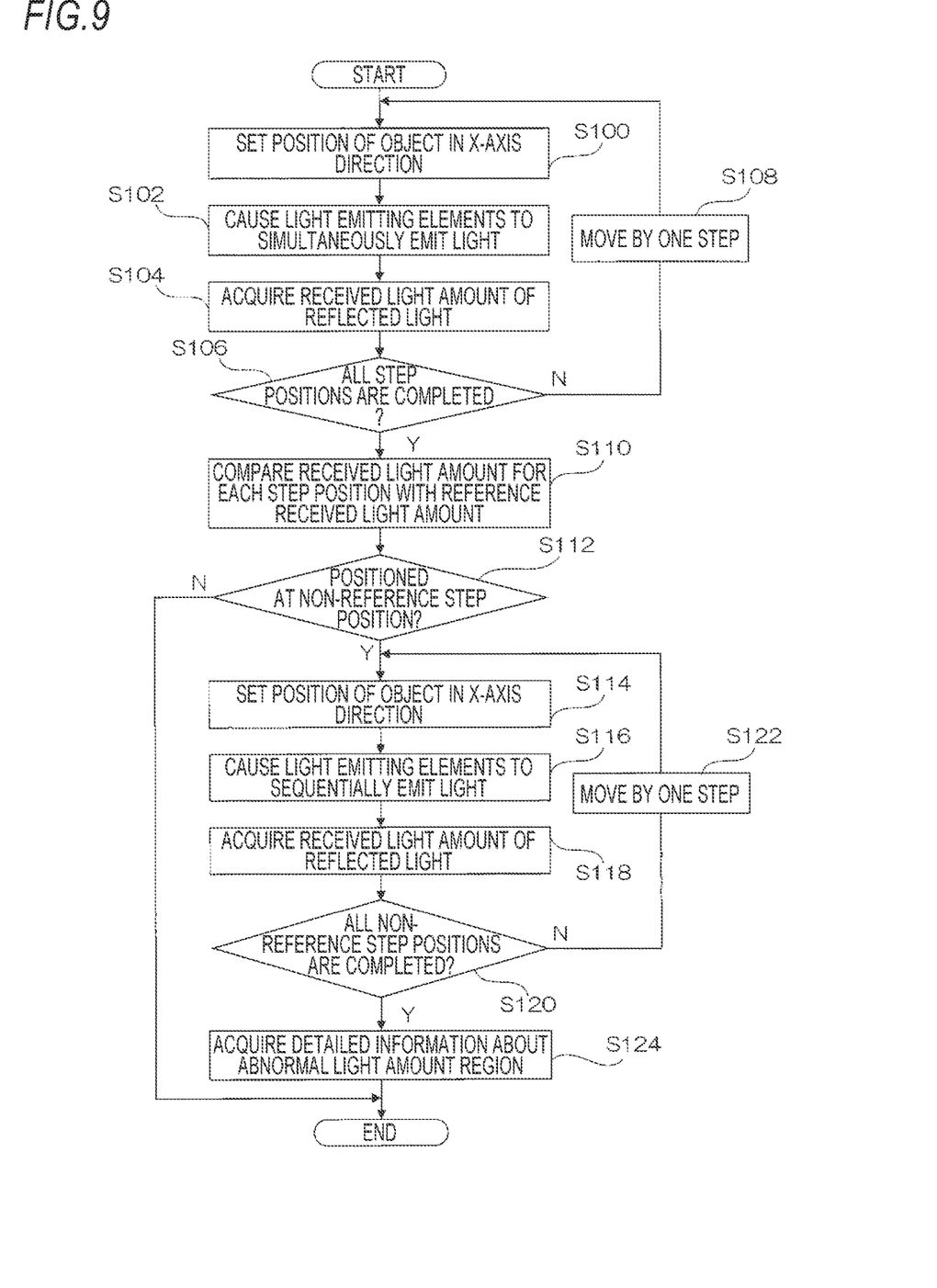
FIG. 9 is a flowchart of a processing flow of an abnormal spot specifying processing program according to the first exemplary embodiment.

Next, an abnormal spot specifying processing program for specifying an abnormal spot by using the measurement apparatus 10 according to the present exemplary embodiment will be described with reference to FIG. 9. FIG. 9 is a flowchart of a processing flow of an abnormal spot specifying processing program according to the present exemplary embodiment. In the processing illustrated FIG. 9, for example, when an instruction of execution start is made by a user through an input unit (not illustrated), the CPU 100 of the controller 20 reads and executes the abnormal spot specifying processing program from a memory unit such as the ROM 102.

As illustrated in FIG. 9, first, in step S100, the position of the object OB in the X-axis direction is set. In the present exemplary embodiment, the movement of the object OB is performed by moving the object OB in the −X direction from the set position in predetermined steps (unit movement distance).

In next step S102, the light emitting elements 12 are caused to simultaneously emit light, so that the overall irradiation is performed. With the overall irradiation, the irradiation lights IF, which correspond to the number of light emitting elements 12, are projected, as parallel lights, to the surface of the object OB. In the simultaneous light emission in this step, all the light emitting elements 12 are turned off after light emission. Of course, the light emitting elements 12 may light emission may be kept until the first measurement is terminated.

In the next step S104, the received light amount of the reflected light RF generated by the irradiation light IF is acquired through the light receiving elements 16.

In next step S106, a determination is made as to whether the acquisition of the received light amount at all the step positions in the X-axis direction is completed. In the case where negative determination is rendered, in step S108, the object is moved in the −X direction by one step so as to return back to step S100, and the overall irradiation is continued. Meanwhile, in the case where affirmative determination is rendered in step S106, the program proceeds to step S110.

In step S110, the received light amount at each step position is compared with a preset reference received light amount. The reference received light amount is a reference for making determination as to whether a certain region is an abnormal light amount region Q, and is given as, for example, the lower limit value of the received light amount. It should be noted that the reference received light amount is not necessarily given in this manner. The reference received light amount may be given as the upper limit value, or both of the lower limit value and the upper limit value. The reference received light amount may be acquired in advance by an experiment, a simulation, and the like, and may be stored in the memory unit such as the ROM 102.

In the next step S112 determination is made as to whether there is any of the received light amounts at respective step positions out of a range of the reference received light amount as a result of the comparison in step S110, that is, whether there is a non-reference step position where the received light amount is out of the range of the reference received light amount. In the case where negative determination is rendered, the abnormal spot specifying processing program is terminated. Meanwhile, in the case where affirmative determination is rendered, the program proceeds to step S114. The non-reference step position may be temporarily stored in the memory unit such as the RAM 104. A non-target step position is given as, for example, an X coordinate, or a range of X coordinates. The steps up to this step correspond to the first measurement.

In step S114, the object OB is moved to the non-reference step position acquired in step S112, and a position of the object OB in the X-axis direction is set.

In the next step S116, individual irradiation is performed on the object OB by causing the light emitting elements 12 to sequentially emit light. In the individual irradiation in this step, all the light emitting elements 12 may be caused to sequentially emit light, or for example, only the light emitting elements 12, which produce the irradiation light IF toward the abnormal light amount region Q, may be caused to sequentially emit light.

In the next step S118, the received light amount of the reflected light RF for each of the irradiation light IF according to the individual irradiation in step S116.

In the next step S120, determination is made as to whether the individual irradiation is completed in respect to all the non-reference step positions. In the case where negative determination is rendered, in step S122, the position of the object OB in the X direction is moved by one step so as to return the program back to step S114, and the individual irradiation is continued. Meanwhile, in the case where affirmative determination is rendered, the program proceeds to step S124.

In step S124, detailed information about the abnormal light amount region Q, that is, information indicating a position, a size, a surface condition, and the like of a defect is acquired based on the received light amount of the reflected light RE acquired in step S118. Thereafter, the abnormal spot specifying processing program ends. The steps up to this step correspond to the second measurement.

Second Exemplary Embodiment

A measurement apparatus according to the present exemplary embodiment will be described with reference to FIG. 10. The present exemplary embodiment is an aspect in which the overall irradiation for the first measurement in the aforementioned exemplary embodiment is changed to divided overall irradiation. Therefore, since the measurement apparatus according to the present exemplary embodiment is identical to the measurement apparatus 10 according to the aforementioned exemplary embodiment, reference will be made to FIGS. 1 and 2 and the like as necessary, and the illustration of the measurement apparatus is omitted.

By the way, in the measurement apparatus 10, basically, even the irradiation light IF from one light emitting element 12 is set such that the light amount of the reflected light RF received by the light receiving elements 16 becomes a light amount sufficient to perform the measurement. Therefore, it is necessary to consider a relationship between a size of a defective region of the object OB and the reflected light amount according to the overall irradiation, or a relationship between a difference between the reflected light amount in the case where a defect exists and the reflected light amount in the case where no reflected light amount exists (i.e., a normal case), and the reflected light amount according to the overall irradiation. That is, for example, when the defective region is small, the reflected light amount determined in consideration of a condition of the defective region, that is, the reflected light amount caused by the abnormal light amount region Q is decreased, but in this case, when all the light emitting elements 12 are caused to simultaneously emit light, it is considered that the reflected light caused by the abnormal light amount region Q is buried in the reflected light according to the simultaneous light emission, and contrast in the abnormal light amount region Q is decreased, and as a result, the precision in specifying a defective position is deteriorated. In addition, it is considered that because the light receiving elements 16 receive light in the reflected lights RF generated by the irradiation lights IF from many light emitting elements 12 are added, an edge of the defect becomes more ambiguous.

Therefore, in the present exemplary embodiment, the light emitting elements 12 are divided into predetermined groups to configure plural light emitting element groups, and the overall irradiation in the first measurement is performed by causing the light emitting element groups to emit light by the light emitting element group unit.

The divided overall irradiation according to the present exemplary embodiment will be described in more detail with reference to FIG. 10. FIG. 10 is a view of spots S (S1 to S18) of the irradiation light IF directed toward the object OB when viewed from the top side of the measurement, apparatus 10 illustrated in FIG. 1, and it is assumed that the number of the light emitting elements 12 is eighteen, as an example.

Figure 10A:
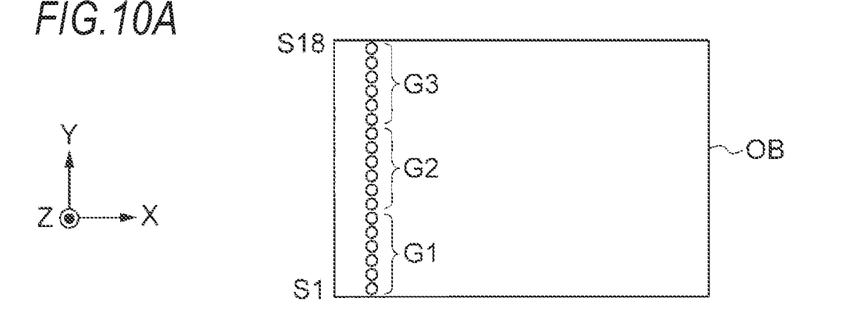
FIGS. 10A to 10D are views for explaining overall irradiation of a measurement apparatus according to a second exemplary embodiment.

FIG. 10A is a view for explaining an example of grouping the light emitting elements 12. That is, in the present exemplary embodiment, the eighteen light emitting elements 12 are divided into three groups, that is, groups G1, G2, and G3, six for each group. The number of grouped light emitting elements 12 may be determined based on a size of the estimated abnormal light amount region Q (a size of a defective region). For example, the light emitting elements 12 may be divided into two groups, nine for each group, in a case where the size of the estimated defective region is large, the light emitting elements 12 may be divided into three groups, six for each group, in a case where the assumed defective region has middle size, and the light emitting elements 12 may be divided into six groups, three for each group, in a case where the size of the assumed defective region is small. In addition, the light emitting elements 12 may be caused to emit light one by one as necessary. That is, the individual irradiation may be performed. As the light emitting elements 12 are grouped based on the aforementioned reference, the number of light emitting elements 12, which simultaneously emit light, is limited such that contrast becomes clearer, and as a result, the precision in specifying a defective region is increased.

In the divided overall irradiation according to the present exemplary embodiment, any one light emitting element group may be caused to emit light, or all the light emitting element groups may be caused to sequentially emit light. The contents of the grouping as described above may be stored in the memory unit such as the ROM 102. In an actual measurement, divided simultaneous light emission by a fixed group may be performed, and the divided simultaneous light emission may be performed by switching the groups each time when the measurement is performed.

Figure 10B:
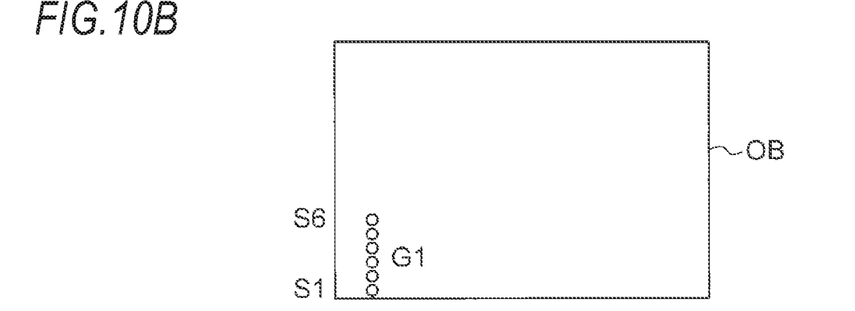
Figure 10C:
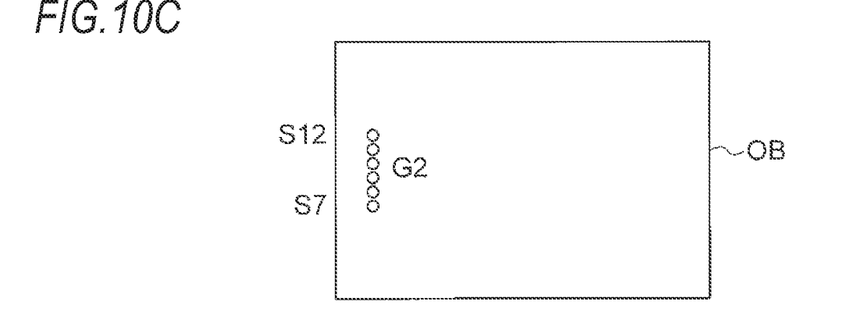
Figure 10D:
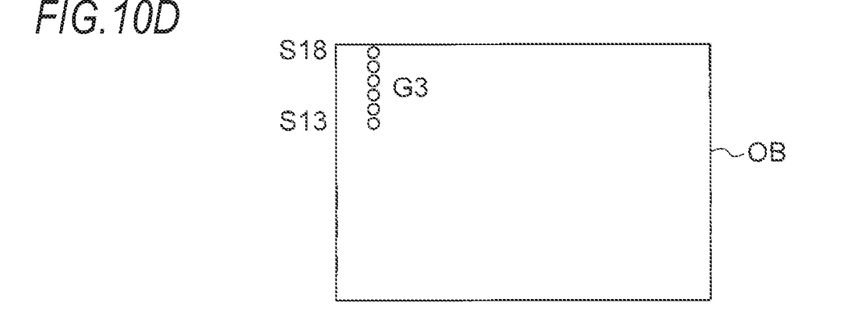

FIGS. 10B to 10D illustrate an operation of the light emitting elements 12 according to the divided simultaneous light emission in a case where all the light emitting element groups are caused to sequentially emit light. That is, as illustrated in FIG. 10B, the group G1 is caused to emit light first, and the light receiving elements 16 receive the reflected light RF according to the divided overall irradiation of the group G1. Next, as illustrated in FIG. 10C, the group G2 is caused to emit light, and the light receiving elements 16 receive the reflected light RF according to the divided overall irradiation of the group G2. Finally, as illustrated in FIG. 10D, the group G3 is caused to emit light, and the light receiving elements 16 receive the reflected light RF according to the divided overall irradiation of the group G3. The received light amounts of the reflected lights RF according to the divided overall irradiation of the groups G1, G2, and G3 are combined by the CPU 100, and determination is made as to whether the abnormal light amount region Q exists using the combined received light amounts.

In a case where the overall irradiation according to the present exemplary embodiment is adopted, the divided simultaneous light emission may be performed in the processing of specifying an abnormal spot in step S102 of the flowchart illustrated in FIG. 8, and the remaining steps are identical to those in the aforementioned exemplary embodiment.

According to the measurement apparatus according to the present exemplary embodiment, a good contrast is secured in a defective region according to the individual divided overall irradiation, and the ability of detecting an edge of the defective region is improved.

According to the divided overall irradiation according to the present exemplary embodiment, the saturation of the light receiving elements 16 is also inhibited at the same time. That is, in the measurement apparatus according to the present exemplary embodiment, as described above, even the irradiation light IF from one light emitting element 12 is set such that the light amount of the reflected light RF received by the light receiving elements 16 becomes a light amount sufficient to perform the measurement. In other words, the light receiving elements 16 are used in a state immediately before the light receiving elements 16 are saturated. Therefore, it may be said that the light receiving elements 16 according to the present exemplary embodiment are easily saturated. However, by using the divided overall irradiation according to the present exemplary embodiment, the saturation of the light receiving elements 16 is also further reduced.

In addition, in the aforementioned exemplary embodiments, descriptions have been made while exemplifying a configuration in which grouping is performed for every successive light emitting elements 12 when the light emitting elements 12 are grouped. It should be noted that the present invention is not limited thereto. For example, when it is considered that the one-hundred light emitting elements 12 of the light emitter 14 are grouped into ten groups, the light emitting elements 12 are grouped into light emitting element groups (1, 2, . . . , 10), (11, 12, . . . , 20), . . . , and (91, 92, . . . , 100) in the aforementioned exemplary embodiment. The numbers in the parentheses are the numbers continuously given to successive light emitting elements 12. For example, the light emitting elements 12 may be grouped by imparting discrete numbers. That is, the light emitting elements 12 may be grouped into light emitting element groups (1, 11, . . . , 91), (2, 12, . . . , 92), . . . , and (10, 20, . . . , 100).

Then, respective light emitting element groups are caused to sequentially and continuously emit light, and the light receiving elements 16 receive each reflected light RF. According to this configuration, an integrated value of the reflected light RF at separate measurement points is received, but in a case where it is determined that an abnormal value exists in the result of each simultaneous light emission, a detailed abnormal region is measured, for example, by causing the light emitting element group (1, 11, . . . , 91) to sequentially emit light again. According to this configuration, it is effective for measuring, for example, a periodic and comparatively long continuous defect.

In addition, in the aforementioned exemplary embodiments, descriptions have been made while exemplifying a configuration in which the contrast of a defective region is increased by adopting divided overall irradiation. It should be noted that the present invention is not limited thereto. For example, in the overall irradiation, an emitted light amount of each of the light emitting elements 12 may be decreased, or a gain of a light receiving circuit connected to the light receiving element 16 may be decreased. The reduction of the emitted light amount of the light emitting elements 12 is adjusted, for example, by an electric current applied to the light emitting elements 12. Or, on the contrary, the emitted light amount of the light emitting elements 12 according to the sequential light emission of the second measurement may be increased, or a gain of the light receiving circuit connected to the light receiving element 16 may be increased.

In addition, the simultaneous light emission performed in the first measurement of each of the aforementioned exemplary embodiments, it is considered that a measurement result becomes inaccurate in a case where there is a variation in the emitted light amount of the plural light emitting elements 12, which constitute the light emitter 14. As a method of dealing with the variation of the emitted light amount, there is, for example, a method of measuring in advance the emitted light amount of each of the light emitting elements 12, and controlling the respective light emitting elements 12 such that the emitted light amounts of the respective light emitting elements 12 become substantially equal to each other during the measurement.

That is, the emitted light amount of each of the light emitting elements 12 is measured in advance by using a reference light receiving element, and the emitted light amount is stored in the memory unit such as the ROM 102. In addition, a driving circuit that operates each of the light emitting elements 12 is configured to be able to control the emitted light amount of each of the light emitting element 12. Further, during the measurement, the driving circuit performs a feedback control for the respective light emitting elements 12 such that the emitted light amount of each of the light emitting elements 12 becomes a predetermined target value, that is, a difference between the target value and the stored emitted light amount from each of the light emitting elements is filled.

Alternatively, for example, as a preprocessing of an actual measurement, the emitted light amount of each of the light emitting elements 12 of the light emitter 14 is measured by the light receiving element 16 disposed on the light receiver 18, and the emitted light amount is stored in the memory unit such as the RAM 104. When the measurement is performed, the light emitting elements 12 may be subjected to a feedback control such that the emitted light amount of each of the light emitting elements 12 becomes a predetermined target value.

In addition, in each of the aforementioned exemplary embodiments, descriptions have been made while exemplifying a configuration in which the object OB is moved when measuring the entire object OB or a part of the object OB. It should be noted that the present invention is not limited thereto. Since the light emitter 14 and the object OB may be moved relative to each other during the measurement of the entire object OB or a part of the object OB, the object OB may be fixed and the light emitter 14 may be moved.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A measurement apparatus comprising:
    a plurality of light emitting units configured to generate irradiation light to be emitted to an object;
    a light receiving unit configured to receive reflected light of the irradiation light that is projected to the object and reflected, and outputs a reflected light amount;
    a drive unit configured to perform a relative movement so as to cause the object and the irradiation light to move relative to each other; and
    a controller configured to perform a control to execute a first measurement and a second measurement, wherein the first measurement includes
        acquiring an overall reflected light amount for the entire object by causing the plurality of light emitting units to simultaneously emit light while performing the relative movement by the drive unit, and
        when an abnormal reflected light amount exists in the overall reflected light amount, specifying an abnormal light amount region of the object corresponding to the abnormal reflected light amount, and
    the second measurement includes
        acquiring a partial reflected light amount of the object in a scanning region that is a partial region of the object at least including the abnormal light amount region, by causing the plurality of light emitting units to sequentially emit light while performing the relative movement by the drive unit in the scanning region, and
        measuring an abnormal region of the object using the partial reflected light amount,
    wherein the light receiving unit is disposed between the plurality of light emitting elements and the object to be measured and the light receiving unit comprises a central aperture to permit light to pass from the plurality of light emitting elements to the object.

2. The measurement apparatus according to claim 1, wherein
    the drive unit is configured to cause the object and the irradiation light to move relative to each other on a unit movement distance basis, and
    the controller performs the relative movement such that the unit movement distance of the relative movement in the second measurement is smaller than that in the first measurement.

3. The measurement apparatus according to claim 1, wherein
    the controller
        specifies the abnormal light amount region in the first measurement as an abnormal range that is a range in at least one of (i) a direction of the relative movement and a direction intersecting the direction of the relative movement, and
        sets the scanning region as a region obtained by adding a predetermined range to the abnormal range.

4. The measurement apparatus according to claim 1, wherein in the first measurement, the controller causes a part of the plurality of light emitting units to simultaneously emit light.

5. The measurement apparatus according to claim 4, wherein the number of the part of the light emitting units is set in accordance with a size of the abnormal region.

6. The measurement apparatus according to claim 4, wherein
    the plurality of light emitting units are grouped into a plurality of light emitting unit groups, and
    the controller performs simultaneous light emission in the first measurement by causing the plurality of light emitting unit groups to sequentially emit light by a light emitting unit group unit.

7. The measurement apparatus according to claim 1, wherein
    the plurality of light emitting units are configured to project the irradiation light to different positions on a surface of the object, respectively, and
    in the second measurement, the controller causes the light emitting units, which are located at positions for projecting the irradiation light to the scanning region among the plurality of light emitting units, to sequentially emit light.

8. The measurement apparatus according to claim 1, wherein the plurality of light emitting units aligned adjacent to one another.

9. The measurement apparatus according to claim 1, wherein the light receiving apparatus unit comprises a plurality of light receiving elements.

* * * * *